United States Patent [19]

Hansen, Jr. et al.

[11] Patent Number: 5,464,843

[45] Date of Patent: Nov. 7, 1995

[54] IMIDAZO[1,2-A]PYRIDINYLDIACID COMPOUNDS FOR COGNITIVE ENHANCEMENT AND FOR TREATMENT OF COGNITIVE DISORDERS AND NEUTROTOXIC INJURY

[75] Inventors: Donald W. Hansen, Jr., Skokie; Karen B. Peterson, Vernon Hills, both of Ill.; Joseph B. Monahan, Black Jack, Mo.

[73] Assignee: G.D. Searle & Co., Chicago, Ill.

[21] Appl. No.: 133,496

[22] Filed: Oct. 8, 1993

Related U.S. Application Data

[63] Continuation of Ser. No. 902,630, Jun. 23, 1992, abandoned.

[51] Int. Cl.[6] .................. C07D 471/04; A61K 31/44
[52] U.S. Cl. .................................. 514/300; 546/121
[58] Field of Search ........................ 546/121; 514/300

[56] References Cited

U.S. PATENT DOCUMENTS

| | | | |
|---|---|---|---|
| 3,359,582 | 11/1970 | Ferrari et al. | 470/195 |
| 4,233,301 | 11/1980 | Baldwin et al. | 514/249 |
| 4,330,543 | 5/1982 | Baldwin et al. | 514/232.5 |
| 4,408,047 | 10/1983 | Baldwin et al. | 544/250 |
| 4,450,164 | 5/1984 | Bristol et al. | 514/303 |
| 4,501,745 | 2/1985 | Kaplan et al. | 514/210 |
| 4,650,796 | 3/1987 | George et al. | 514/213 |
| 4,997,821 | 3/1991 | Cordi et al. | 514/82 |

FOREIGN PATENT DOCUMENTS

| | | |
|---|---|---|
| 0033094A1 | 1/1981 | European Pat. Off. . |
| 0120589A1 | 2/1984 | European Pat. Off. . |
| 0394905A2 | 4/1990 | European Pat. Off. . |
| 0398283A1 | 5/1990 | European Pat. Off. . |
| 0420806A1 | 9/1990 | European Pat. Off. . |
| 2638161 | 4/1990 | France . |
| WO89/03833 | 5/1989 | WIPO . |

OTHER PUBLICATIONS

S. M. Rothman et al, *Ana Neurol*, 19:105–111, 1986.
J. W. Johnson et al, *Nature*, 325:529–531, 1987.
D. Graham et al, *Biochemistry*, 24:990–994, 1985.
H. Kishimoto et al, *Jour. of Neuro.*, 37(4):1015–1024, 1981.
L. Nguyen et al, *Excit.Amino Acids: Receptor.II*, Abstract No. 209.16.
J. B. Monahan et al, *Pharm. Bio. & Behav.*, 34:649–653, 1989.
G. E. Handelmann et al, *Pharm. Bio. & Behav.*, 34:823–828, 1989.
S. I. Deutsch et al, *Clin. Neuro.*, 12(1): 1–13, 1989.
P. C. Contreras et al, *Mole. Neurobio.*, 1:191–211, 1987.
C. Casagrande et al, *Il. Farmaco-Ed. Sc.*, 23:1141–1148, 1968.

Primary Examiner—Alan L. Rotman
Attorney, Agent, or Firm—Joseph W. Bulock; J. Timothy Keane

[57] ABSTRACT

A class of imidazo[1,2-a]pyridinyldiacid compounds is described for cognitive enhancement and for treatment of cognitive disorders and which have activity as a cognitive enhancer. Such compounds are also useful to reduce neurotoxic injury associated with anoxia or ischemia which typically follows stroke, cardiac arrest or perinatal asphyxia. The treatment includes administration of a compound of this class alone or in a composition in an amount effective as an agonist or partial agonist to modulate, or as an antagonist to inhibit, excitotoxic actions at major neuronal excitatory amino acid receptor sites. Compounds of most interest are those of the formula:

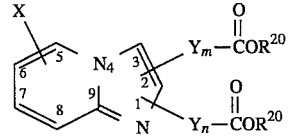

wherein each $R^{20}$ is independently selected from hydrogen, methyl, ethyl, n-propyl, isopropyl, n-butyl, isobutyl, sec-butyl, tert-butyl, cyclopropyl, cyclobutyl, cyclopentyl, cyclohexyl and cycloheptyl; wherein each of $Y_m$ and $Y_n$ is a spacer group selected from methylene and ethylene radicals; wherein m is an integer of one or two; wherein n is an integer of from zero to two; wherein X is one or more groups independently selected from hydrogen, alkyl, cycloalkyl, halo, haloalkyl, hydroxy, hydroxyalkyl, alkoxy, alkoxyalkyl and alkanoyl; or a pharmaceutically-acceptable salt thereof.

4 Claims, No Drawings

IMIDAZO[1,2-A]PYRIDINYLDIACID COMPOUNDS FOR COGNITIVE ENHANCEMENT AND FOR TREATMENT OF COGNITIVE DISORDERS AND NEUTROTOXIC INJURY

This is a continuation of application Ser. No. 07/902,630 filed Jun. 23, 1992, now abandoned.

FIELD OF THE INVENTION

This invention is in the field of clinical neurology and relates specifically to a class of compounds, compositions and methods for cognitive enhancement and for treatment of cognitive disorders. The subject compounds and compositions are also useful for neuroprotective purposes such as controlling chronic or acute neurotoxic injury or brain damage resulting from neurodegenerative diseases. For example, these compounds and compositions are particularly useful for treating neurotoxic injury which follows periods of anoxia or ischemia associated with stroke, cardiac arrest or perinatal asphyxia. The compounds and compositions of the invention would also be useful as anticonvulsants and analgesics.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman et al, al, *Annals of Neurology*, Vol. 19, No. 2 (1986)].

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia. Agents which selectively act as agonists and stimulate binding can enhance cognition and can be used to treat cognitive disorders.

Glycine, alanine and serine have been shown to enhance the electrophysiological response induced by NMDA in cortical neurons [see J. W. Johnson et al, *Nature*, 325, 529 (1987)]. This potentiation has been shown to be independent of the strychnine-sensitive glycine receptor [see D. Grahm et al, *Biochemistry*, 24, 990 (1985)]. A strychnine-insensitive, sodium independent [$^3$H]glycine recognition site has been identified [see H. Kishimoto et al, *J. Neurochem.*, 37, 1010 (1981)] and a correlation has been established between the regional distribution of [$^3$H]glycine and NMDA-sensitive L-[3H]glutamate binding sites [L. Nguyen et al, *Abs. Soc, Neurosci.*, 13, 759 (1987)].

Compounds which interact with the glycine receptor have been demonstrated to enhance the performance of learning tasks in rats, thereby suggesting that glycine agonists are useful as cognitive enhancers [J. B. Monahan et al, *Pharmacol. Blochem. Behav.*, 34, 349 (1989); G. E. Handelmann et al, *Pharmacol. Blochem. Behav.*, 34, 823 (1989)] as well as antipsychotic agents [S. I. Deutsch, *Neuropharmacol.*, 12, 1 (1989)].

It has been shown that the glycine receptor site is functionally linked to both the NMDA receptor site, as well as the phencyclidine (PCP) receptor site [see, for example, P. C. Contreras, *Molec. Neurobiol.*, 1, 191 (1987)]. Thus, compounds which manifest an agonist effect on the NMDA/ glycine/PCP receptor complex, i.e., compounds which positively modulate the receptor complex, can be used to treat cognitive disorders and/or for cognitive enhancement. Compounds which manifest an antagonist effect, both competitive and non-competitive, can be used as neuroprotective agents, anticonvulsants, muscle relaxants and anxiolytics.

Several classes of imidazopyridine compounds having various pharmaceutical uses are known. For example, EP#120,589, published 3 Oct. 1984, describes certain imidazo-(1,2-a)pyridinylheterocyclic compounds for use as cardiotonic and antiulcer agents. Schering EP#33,094 published 5 Aug. 1981, describes 3,8-disubstituted-imidazo-( 1,2-a)pyridine compounds for use as antisecretory and cytoprotective agents. Syntheiabo U.S. Pat. No. 4,650,796, published 19 Feb. 1986, describes 2-phenyl-3-acylaminomethylimidazoDyridine compounds as anxiolytic, hypnotic and anticonvulsant agents. Synthelabo U.S. Pat. No. 4,501,745 describes imidazo-(1,2-a)pyridinealkanoic acid derivatives as anxiolytic, hypnotic and anticonvulsant agents. Schering U.S. Pat. No. 4,450,164 describes phosphonic acid derivatives of imidazo(1,2-a)-pyridine compounds for use as treatment of gastrointestinal diseases such as ulcers. Siphar U.S. Pat. No. 3,539,582 discloses imidazo-(1,2-a)-pyridine- 2,3-dicarboxylic acid and the corresponding esters and amides thereof having analeptic properties. [See also Casagrande et al, *Farmaco. Ed. Sci.* 23(12), 1141 (1968) for treating respiratory infections.] Asssle WO8903-833-A discloses 5-hydroxy-imidazo-(1,2-a) pyridine-2-ethylcarboxylate-3 -carboxylic acid useful for treating osteoporosis. Merck U.S. Pat. No. 4,408,047 discloses substituted imidazo-(1,2 -a)-pyridine-2,3-dicarboxylic acids and carboxylates having β-adrenergic blocking activity. Merrell Dow EP #0394905 published 31 Oct. 1990, discloses carboxyindoles as NMDA antagonists, one such carboxyindole being 3-(2-carboxy-6 -chloro-indol-3-yl)propionic acid.

DESCRIPTION OF THE INVENTION

Control of neuropathological processes and the neurodegenerative consequences thereof in mammals is provided by treating a mammal susceptible to neurotoxic injury with an anti-excitotoxic effective amount of a compound characterized by having activity as an antagonist at a major neuronal excitatory amino acid receptor site, such as at the NMDA/ glycine/PCP receptor complex, such as at the NMDA receptor site. Treatment of cognitive disorders and enhancement of cognitive functions in mammals is also provided by treating a mammal with a cognitive enhancing amount of a compound characterized by having activity as an agonist or partial agonist at a major neuronal excitatory amino acid receptor site, such as at the NMDA/glycine/PCP receptor complex, such as at the glycine receptor site.

Such compounds may be selected from a class of imidazo[1,2-a]pyridinyldiacid compounds defined by Formula I:

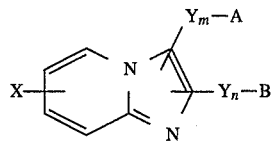

wherein each of A and B is a moiety independently selected from carboxylic acid, tetrazole, phosphorus-containing acids and sulfur-containing acids and the amide, ester and salt derivatives of said acids; each of $Y_m$ and $Y_n$ is a spacer group independently selected from one or more of alkyl, cycloalkyl, cycloalkylalkyl, alkenyl, alkynyl, aryl and aralkyl radicals; m is an integer of from one to five, inclusive; n is an integer of from zero to five, inclusive; and X represents one or more groups selected from hydrogen, alkyl, cycloalkyl, cycloalkylalkyl, halo, haloalkyl, alkenyl, cycloalkenyl, alkynyl, aryl, aralkyl, hydroxy, hydroxyalkyl, alkoxy, alkoxyalkyl, atkoxycarbonyl, aralkoxy, aralkylthio, cyano, nitro, alkanoyl, alkylthio, arylthio, alkylsulfinyl, arylsulfinyl, alkylsulfonyl, arylsulfonyl, and amino and amido radicals of the formula:

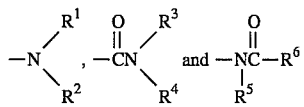

wherein each of $R^1$, $R^2$, $R^3$, $R^4$, $R^5$ and $R^6$ is independently selected from hydrogen, alkyl, cycloalkyl, hydroxyalkyl, cycloalkylalkyl, alkoxyalkyl, aralkyt and aryl; or a pharmaceutically-acceptable salt thereof.

A preferred class consists of compounds within Formula I wherein each of A and B is a moiety independently selected from

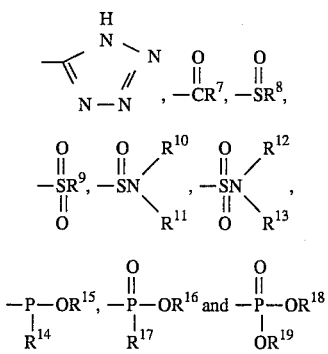

wherein each of $R^7$ through $R^{19}$ is independently selected from hydrogen, alkyl, allyl, cycloalkyl, cycloalkylalkyl, aryl and aralkyl, with the proviso that each of $R^7$, $R^8$ and $R^9$ cannot be hydrogen; wherein each of $R^7$, $R^8$ and $R^9$ is further independently selected from $OR^{20}$ wherein $R^{20}$ is selected from hydrogen, alkyl, cycloalkyl, cycloalkylalkyl, aryl and aralkyl; wherein each of $R^7$, $R^8$, $R^9$, $R^{11}$, $R^{13}$, $R^{14}$ and $R^{17}$ is further independently selected from an amino radical of the formula

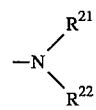

wherein each of $R^{21}$ and $R^{22}$ is independently selected from hydrogen, alkyl, cycloalkyl, hydroxy, hydroxyalkyl, haloalkyl, cycloalkylalkyl, alkoxyalkyl, aralkyl and aryl with the proviso that $R^{21}$ and $R^{22}$ cannot both be hydroxy; wherein each of $R^{14}$ and $R^{17}$ my be further independently selected from hydroxy, alkoxy, alkylthio, aryloxy, arylthio, aralkylthio and aralkoxy;

each of $Y_m$ and $Y_n$ is a spacer group independently selected from one or more of alkyl, cycloalkyl, cycloalkylalkyl, alkenyl, alkynyl, aryl and aralkyl radicals; m is an integer of from one to five, inclusive; n is an integer of from zero to five, inclusive;

wherein X represents one or more groups selected from hydrogen, alkyl, cycloalkyl, cycloalkylalkyl, halo, haloalkyl, alkenyl, cycloalkenyl, alkynyl, aryl, aralkyl, hydroxy, hydroxyalkyl, alkoxy, alkoxyalkyl, alkoxycarbonyl, aralkoxy, aralkylthio, cyano, nitro, alkanoyl, alkylthio, arylthio, alkylsulfinyl, arylsulfinyl, alkylsulfonyl, arylsulfonyl, and amino and amido radicals of the formula:

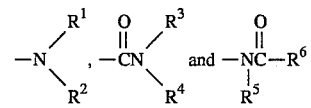

wherein each of $R^1$, $R^2$, $R^3$, $R^4$, $R^5$ and $R^6$ is independently selected from hydrogen, alkyl, cycloalkyl, hydroxyalkyl, cycloalkylalkyl, alkoxyalkyl, phenalkyl and phenyl, and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may further contain one or more hetero atoms as ring members selected from oxygen, nitrogen and sulfur and which heterocyclic group may be saturated or partially unsaturated; wherein $R^1$ and $R^2$ taken together and $R^3$ and $R^4$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur; or a pharmaceutically-acceptable acid addition salt thereof.

An even more preferred class consists of compounds within Formula I wherein each of A and B is a moiety independently selected from

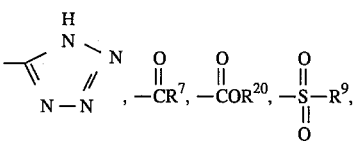

-continued

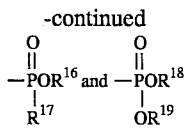

wherein each of $R^7$, $R^9$, $R^{16}$, $R^{17}$, $R^{18}$, $R^{19}$ and $R^{20}$ is independently selected from hydrogen, alkyl, cycloalkyl, cycloalkylalkyl, phenyl and benzyl with the proviso that $R^7$ and $R^9$ cannot be hydrogen; and wherein each of $R^7$, $R^9$ and $R^{17}$ is further selected from amino radicals of the formula

wherein each of $R^{21}$ and $R^{22}$ is independently selected from hydrogen, alkyl, cycloalkyl, cycloalkylalkyl, phenyl and benzyl;
each of $Y_m$ and $Y_n$ is a spacer group independently selected from one or more of alkyl, cycloalkyl, cycloalkylalkyl, alkenyl, alkynyl, aryl and aralkyl radicals; m is an integer of from one to five, inclusive; n is an integer of from zero to five, inclusive;
wherein X represents one or more groups selected from hydrogen, alkyl, cycloalkyl, cycloalkylalkyl, halo, haloalkyl, alkenyl, cycloalkenyl, alkynyl, aryl, aralkyl, hydroxy, hydroxyalkyl, alkoxy, alkoxyalkyl, alkoxycarbonyl, aralkoxy, aralkylthio, cyano, nitro, alkanoyl, alkylthio, arylthio, alkylsulfinyl, arylsulfinyl, alkylsulfonyl, arylsulfonyl, and amino and amido radicals of the formula:

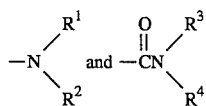

wherein each of $R^1$, $R^2$, $R^3$ and $R^4$ is independently selected from hydrogen, alkyl, phenyl and benzyl; or a pharmaceutically-acceptable salt thereof.

A first subset of highly preferred compounds consists of those within Formula I selected from compounds of Formula II

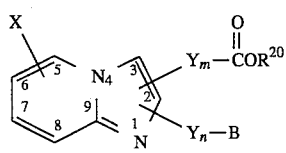

(II)

wherein B is selected from

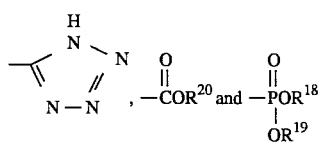

wherein each of $R^{18}$, $R^{19}$ and $R^{20}$ is selected from hydrogen, alkyl, allyl, cycloalkyl, cycloalkylalkyl, phenyl and benzyl; wherein each of $Y_m$ and $Y_n$ is a spacer group independently selected from one or more groups of the formula

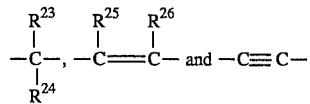

wherein each of $R^{23}$ and $R^{24}$ is independently selected from hydrogen, alkyl, cycloalkyl, halo, haloalkyl, phenyl, benzyl, hydroxy, hydroxyalkyl, alkoxy, phenoxy, alkoxyalkyl, benzyloxy, cyano, alkanoyl,

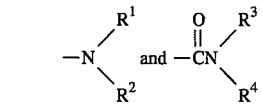

wherein each of $R^1$, $R^2$, $R^3$ and $R^4$ is independently selected from hydrogen, alkyl and phenyl; wherein $R^{23}$ and $R^{24}$ may be taken together to form oxo; wherein each of $R^{25}$ and $R^{26}$ is independently selected from hydrogen, alkyl, haloalkyl, phenyl, hydroxyalkyl and alkoxyalkyl; wherein m is an integer of from one to three, inclusive; n is an integer of from zero to three, inclusive;
wherein X is one or more groups independently selected from hydrogen, alkyl, cycloalkyl, cycloalkylalkyl, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, alkanoyl, mercapto, alkylthio, arylthio, alkylsulfinyl, alkylsulfonyl, arylsulfinyl and arylsulfonyl,

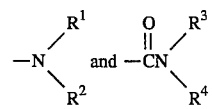

wherein each of $R^1$, $R^2$, $R^3$ and $R^4$ is independently selected from hydrogen, alkyl and phenyl; or a pharmaceutically-acceptable salt thereof.

A more highly preferred class of compounds within the first subset defined by Formula II consists of compounds of Formula III

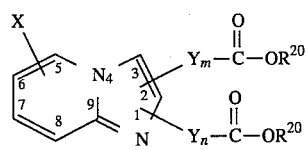

(III)

wherein each $R^{20}$ is independently selected from hydrogen, alkyl, allyl, cycloalkyl, cycloalkylalkyl, phenyl and benzyl; wherein each of $Y_m$ and $Y_n$ is a spacer group independently selected from one or more groups of the formula

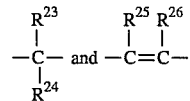

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

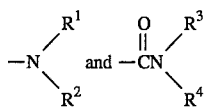

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; m is an integer of from one to three, inclusive; n is an integer of from zero to three, inclusive;

wherein X is one or more groups independently selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

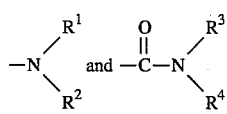

wherein each of $R^1$, $R^2$, $R^3$ and $R^4$ is independently selected from hydrogen and alkyl; or a pharmaceutically-acceptable salt thereof.

Specific compounds of particular interest within Formula III are the following:

7-bromo-2-carboxy-α-methoxyimidazo[1,2-a]pyridine-3-acetic acid
7-bromo-2-carboxy-α-methoxyimidazo[1,2-a]pyridine-3-propanoic acid
7-chloroimidazo[1,2-a]pyridine-2,3-dicarboxylic acid
2-carboxy-7-chloroimidazo[1,2-a]pyridine-3-acetic acid
2-carboxy-7-chloroimidazo[1,2-a]pyridine-3-propanoic acid
7-chloroimidazo[1,2-a]pyridine-2,3-diacetic acid Another more highly preferred class of compounds within the first subset of compounds defined by Formula II consists of compounds of Formula IV

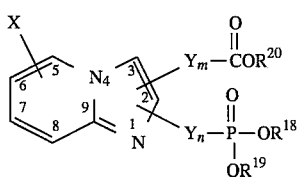

wherein each of $R^{18}$, $R^{19}$ and $R^{20}$ is independently selected from hydrogen, methyl, ethyl, n-propyl, isopropyl, n-butyl, isobutyl, sec-butyl, tert-butyl, cyclopropyl, cyclobutyl, cyclopentyl, cyclohexyl and cycloheptyl;

wherein each of $Y_m$ and $Y_n$ is a spacer group independently selected from one or more groups of the formula

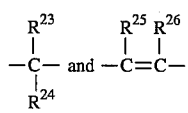

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

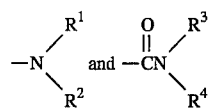

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; wherein m is an integer of from one to three, inclusive; n is an integer of from zero to three, inclusive;

wherein each X is one or more groups selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

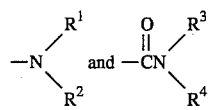

wherein each of $R^1$, $R^2$, $R^3$ and $R^4$ is independently selected from hydrogen and alkyl; or a pharmaceutically-acceptable salt thereof.

Specific compounds of particular interest within Formula IV are the following:

7-bromo-α-hydroxy-2-phosphonoimidazo[1,2-a]pyridine-3-acetic acid
7-bromo-α-hydroxy-2-phosphonoimidazo[1,2-a]pyridine-3 propanoic acid
7-chloro-2-phosphonoimidazo[1,2-a]pyridine-3-carboxylic acid
7-chloro-2-phosphonoimidazo[1,2-a]pyridine-3-acetic acid
7-chloro-2-phosphonoimidazo [1,2-a]pyridine-3-propanoic acid
7-chloro-2-(phosphonomethyl)imidazo[1,2-a]pyridine-3-acetic acid
and the pharmaceutically-acceptable salts thereof.

Another more highly preferred class of compounds within the first subset defined by Formula II consists of compounds of Formula V

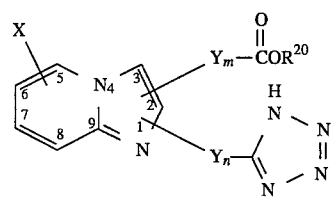

wherein $R^{20}$ is selected from hydrogen, methyl, ethyl, n-propyl, isopropyl, n-butyl, isobutyl, sec-butyl, tert-butyl, cyclopropyl, cyclobutyl, cyclopentyl, cyclohexyl and cycloheptyl;

wherein each of $Y_m$ and $Y_n$ is a spacer group independently selected from one or more groups of the formula

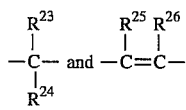

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

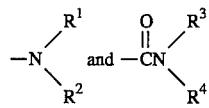

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; wherein m is an integer of from one to three, inclusive; n is an integer of from zero to three, inclusive;

wherein each X is one or more groups selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

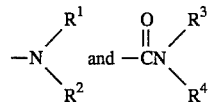

wherein each of $R^1$, $R^2$, $R^3$ and $R^4$ is independently selected from hydrogen and alkyl; or a pharmaceutically-acceptable salt thereof.

Specific compounds of particular interest within Formula V are the following:

7-chloro-α-hydroxy-2-(1H-tetrazol-5-yl)imidazo[1,2-a]pyridine- 3-acetic acid
7-chloro-α-hydroxy-2-(1H-tetrazol-5-yl)imidazo[1,2-a]pyridine- 3-propanoic acid
7-chloro-2-(1H-tetrazol-5-yl)imidazo[1,2-a]pyridine-3-carboxylic acid
7-chloro-2-(1H-tetrazol-5-yl)imidazo[1,2-a]pyridine-3-acetic acid
7-chloro-2-(1H-tetrazol-5-yl) imidazo[1,2-a]pyridine-3-propanoic acid
7 -chloro-2-(1H- tetrazol-5-ylmethyl)imidazo[1,2-a]pyridine-3-acetic acid
and the pharmaceutically-acceptable salts thereof.

A second subset of highly preferred compounds consists of those compounds within Formula I selected from compounds of Formula VI

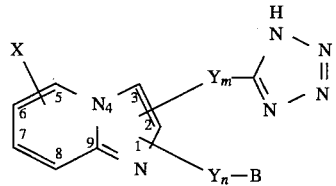

wherein B is selected from

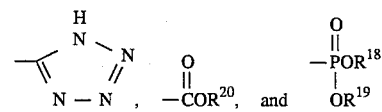

wherein each of $R^{18}$, $R^{19}$ and $R^{20}$ is independently selected from hydrogen, alkyl, cycloalkyl, cycloalkylalkyl, phenyl and benzyl;

wherein each of $Y_m$ and $Y_n$ is a spacer group independently selected from one or more groups of the formula

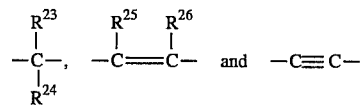

wherein each of $R^{23}$ and $R^{24}$ is independently selected from hydrogen, alkyl, cycloalkyl, halo, haloalkyl, phenyl, benzyl, hydroxy, hydroxyalkyl, alkoxy, phenoxy, alkoxyalkyl, benzyloxy, cyano, alkanoyl,

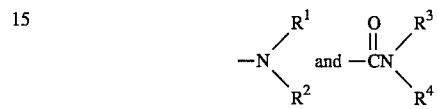

wherein each of $R^i$, $R^2$, $R^3$ and $R^4$ is independently selected from hydrogen, alkyl and phenyl; wherein $R^{23}$ and $R^{24}$ may be taken together to form oxo; wherein each of $R^{25}$ and $R^{26}$ is independently selected from hydrogen, alkyl, haloalkyl, phenyl, hydroxyalkyl and alkoxyalkyl; wherein m is an integer of from one to three, inclusive; n is an integer of from zero to three, inclusive;

wherein X is one or more groups independently selected from hydrogen, alkyl, cycloalkyl, cycloalkylalkyl, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, alkanoyl, mercapto, alkylthio, arylthio, alkylsulfinyl, alkylsulfonyl, arylsulfinyl and arylsulfonyl,

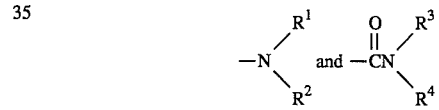

wherein each of $R^1$, $R^2$, $R^3$ and $R^4$ is independently selected from hydrogen, alkyl and phenyl; or a pharmaceutically acceptable salt thereof.

A more highly preferred class of compounds within the second subset defined by Formula VI consists of compounds of Formula VII

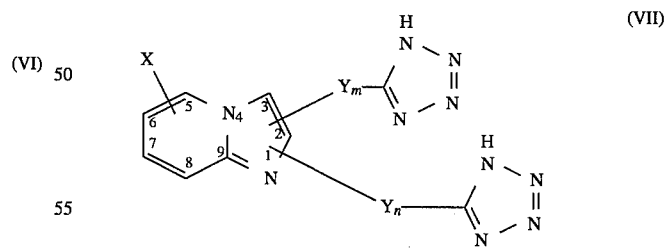

wherein each of $Y_m$ and $Y_n$ is a spacer group independently selected from one or more groups of the formula

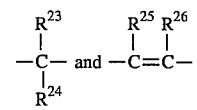

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

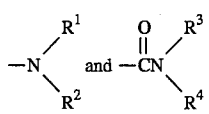

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; m is an integer of from one to three, inclusive; n is an integer of from zero to three, inclusive;

wherein X is one or more groups independently selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

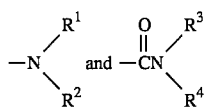

wherein each of $R^1$, $R^2$, $R^3$ and $R^4$ is independently selected from hydrogen and alkyl; or a pharmaceutically-acceptable salt thereof.

Specific compounds of particular interest within Formula VII are the following:

7-chloro-α,2-bis(1H-tetrazol-5-yl)imidazo[1,2-a]pyridine-3-methanol 7-chloro-α,2-bis(1H-tetrazol-5-yl)imidazo[1,2-a]pyridine-3-ethanol 7-chloro-2,3-bis(1H-tetrazol-5-yl)imidazo[1,2-a]pyridine 7-chloro-2-(1H-tetrazol-5-yl)-3-(1H-tetrazol-5-ylmethyl)imidazo[1,2-a]pyridine 7-chloro-2-(1H-tetrazol-5-yl)-3-[2-(1H-tetrazol-5-yl)ethyl]imidazo[1,2-a]pyridine 7-chloro-2,3-bis (1H-tetrazol-5-ylmethyl)imidazo[1,2-a]pyridine and the pharmaceutically-acceptable salts thereof.

Another more highly preferred class of compounds within the second subset defined by Formula VI consists of compounds of Formula VIII

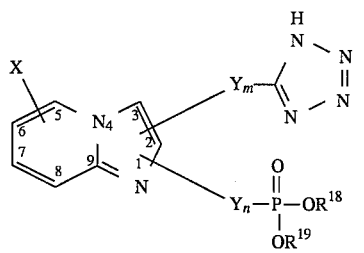

(VIII)

wherein each of $R^{18}$ and $R^{19}$ is independently selected from hydrogen, methyl, ethyl, n-propyl, isopropyl, n-butyl, isobutyl, sec-butyl, tert-butyl, cyclopropyl, cyclobutyl, cyclopentyl, cyclohexyl and cycloheptyl;

wherein each of $Y_m$ and $Y_n$ is a spacer group independently selected from one or more groups of the formula

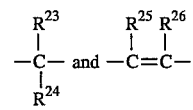

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

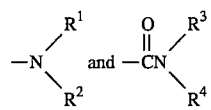

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; wherein m is an integer of from one to three, inclusive; n is an integer of from zero to three, inclusive;

wherein each X is one or more groups selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

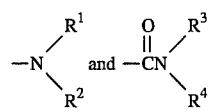

wherein each of $R^1$, $R^2$, $R^3$ and $R^4$ is independently selected from hydrogen and alkyl; or a pharmaceutically-acceptable salt thereof.

Specific compounds of particular interest within Formula VIII are the following:

[7-bromo-3-[methoxy(1H-tetrazol-5-yl)methyl]imidazo[1,2-a] pyridin-2-yl]phosphonic acid

[7-bromo-3-[2-methoxy-2-(1H-tetrazol-5-yl)ethyl]imidazo[1,2-a] pyridin-2-yl]phosphonic acid

[7-chloro-3-(1H-tetrazol-5-yl)imidazo[1,2-a]pyridin-2-yl] phosphonic acid

[7-chloro-3-(1H-tetrazol-5-ylmethyl)imidazo[1,2-a]pyridin-2-yl] phosphonic acid

[7-chloro-3-[2-(1H-tetrazot -5-yl)ethyl]imidazo[1,2-a]pyridin- 2-yl]phosphonic acid

[7-chloro-3-(1H-tetrazol-5-ylmethyl)imidazo[1,2-a]pyridin-2-yl] methyl]phosphonic acid and the pharmaceutically-acceptable salts thereof.

Another more highly preferred class of compounds within the second subset defined by Formula VI consists of compounds of Formula IX

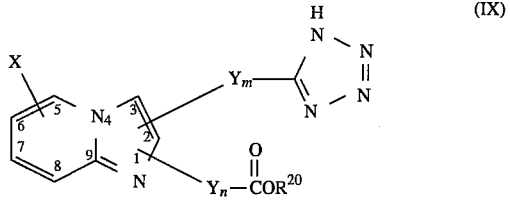

(IX)

wherein each $R^{20}$ is independently selected from hydrogen, methyl, ethyl, n-propyl, isopropyl, n-butyl, isobutyl, sec-butyl, tert-butyl, cyclopropyl, cyclobutyl, cyclopentyl, cyclohexyl and cycloheptyl;
wherein each of $Y_m$ and $Y_n$ is a spacer group independently selected from one or more groups of the formula

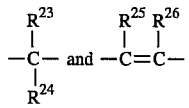

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

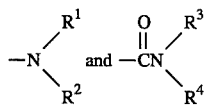

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; wherein m is an integer of from one to three, inclusive; n is an integer of from zero to three, inclusive;
wherein each X is one or more groups selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

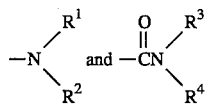

wherein each of $R^1$, $R^2$, $R^3$ and $R^4$ is independently selected from hydrogen and alkyl; or a pharmaceutically-acceptable salt thereof.

Specific compounds of particular interest within Formula IX are the following:
7-bromo-3-[hydroxy{1H-tetrazol-5-yl)methyl]imidazo[1, 2a] pyridine-2-carboxylic acid
7-bromo-3-[2-hydroxy-2-(1H-tetrazol-5-yl)ethyl]imidazo [1,2a] pyridine-2-carboxylic acid
7-chloro-3-(1H-tetrazol-5-yl)imidazo[1,2-a]pyridine-2-carboxylic acid
7-chloro-3-(1H-tetrazol-5-ylmethyl)imidazo[1,2 -a]pyridine-2-carboxylic acid
7-chloro-3-[2 -(1H-tetrazol-5-yl)ethyl]imidazo[1,2 -a]pyridine- 2-carboxylic acid
7-chloro-3-(1H-tetrazol-5-ylmethyl)imidazo[1,2-a]pyridine-2-acetic acid
and the pharmaceutically-acceptable salts thereof.

A third subset of highly preferred compounds consists of those compounds within Formula I selected from compounds of Formula X

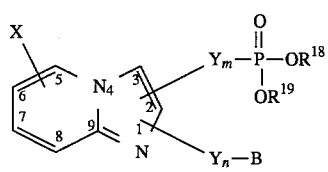

(X)

wherein B is selected from

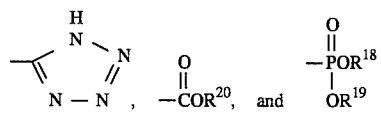

wherein each of $R^{18}$, $R^{19}$ and $R^{20}$ is independently selected from hydrogen, alkyl, cycloalkyl, cycloalkylalkyl, phenyl and benzyl;
wherein each of $Y_m$ and $Y_n$ is a spacer group independently selected from one or more groups of the formula

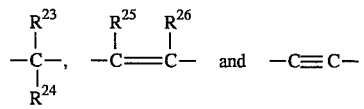

wherein each of $R^{23}$ and $R^{24}$ is independently selected from hydrogen, alkyl, cycloalkyl, halo, haloalkyl, phenyl, benzyl, hydroxy, hydroxyalkyl, alkoxy, phenoxy, alkoxyalkyl, benzyloxy, cyano, alkanoyl,

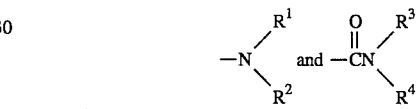

wherein each of $R^1$, $R^2$, $R^3$ and $R^4$ is independently selected from hydrogen, alkyl and phenyl; wherein $R^{23}$ and $R^{24}$ may be taken together to form oxo; wherein each of $R^{25}$ and $R^{26}$ is independently selected from hydrogen, alkyl, haloalkyl, phenyl, hydroxyalkyl and alkoxyalkyl; wherein m is an integer of from one to three, inclusive; n is an integer of from zero to three, inclusive;
wherein X is one or more groups independently selected from hydrogen, alkyl, cycloalkyl, cycloalkylalkyl, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, alkanoyl, mercapto, alkylthio, arylthio, alkylsulfinyl, alkylsulfonyl, arylsulfinyl and arylsulfonyl,

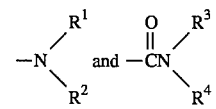

wherein each of $R^1$, $R^2$, $R^3$ and $R^4$ is independently selected from hydrogen, alkyl and phenyl; or a pharmaceutically-acceptable salt thereof.

A more preferred class of compounds within the third subset defined by Formula X consists of compounds of Formula XI

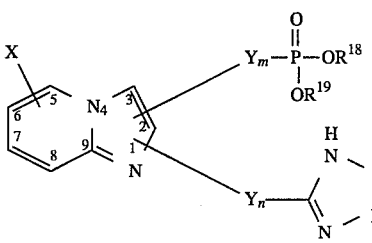

(XI)

wherein each of $R^{18}$ and $R^{19}$ is independently selected from hydrogen, methyl, ethyl, n-propyl, isopropyl, n-butyl, isobutyl, sec-butyl, tert-butyl, cyclopropyl, cyclobutyl, cyclopentyl, cyclohexyl and cycloheptyl;

wherein each of $Y_m$ and $Y_n$ is a spacer group independently selected from one or more groups of the formula

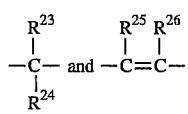

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

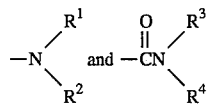

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; wherein m is an integer of from one to three, inclusive; n is an integer of from zero to three, inclusive;

wherein each X is one or more groups selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

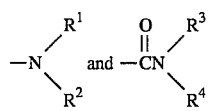

wherein each of $R^1$, $R^2$, $R^3$ and $R^4$ is independently selected from hydrogen and alkyl; or a pharmaceutically-acceptable salt thereof.

Specific compounds of particular interest within Formula XI are the following:

[[6-chloro-2-(1H-tetrazol-5-yl)imidazo[1,2-a]pyridin-5-yl] hydroxymethyl]phosphonic acid;
[[7-bromo-2-(1H-tetrazol-5-yl)imidazo[1,2-a]pyridin-3-yl] hydroxymethyl]phosphonic acid;
[2- [7-bromo-2-(1H-tetrazol-5-yl)imidazo[1,2-a]pyridin-3-yl]-1-hydroxyethyl] phosphonic acid;
[7-chloro-2-(1H-tetrazol-5-yl)imidazo[1,2-a]pyridin-3-yl] phosphonic acid;
[[7-chloro-2-(1H-tetrazol-5-yl)imidazo[1,2-a]pyridin-3-yl] methyl]phosphonic acid;
[2-[7-chloro-2-(1H-tetrazol-5-yl)imidazo[1,2-a]pyridin-3-yl] ethyl]phosphonic acid;
7-chloro-2-(1H-tetrazol-5-ylmethyl)imidazo[1,2-a]pyridin-3-yl] methyl]phosphonic acid;
and the pharmaceutically-acceptable salts thereof.

Another more preferred class of compounds within the third subset defined by Formula X consists of compounds of Formula XII

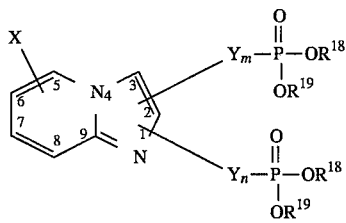

(XII)

wherein each of $R^{18}$ and $R^{19}$ is independently selected from hydrogen, methyl, ethyl, n-propyl, isopropyl, n-butyl, isobutyl, sec-butyl, tert-butyl, cyclopropyl, cyclobutyl, cyclopentyl, cyclohexyl and cycloheptyl;

wherein each of $Y_m$ and $Y_n$ is a spacer group independently selected from one or more groups of the formula

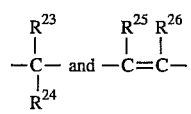

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

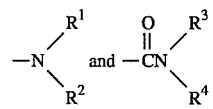

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; wherein m is an integer of from one to three, inclusive; n is an integer of from zero to three, inclusive;

wherein each X is one or more groups selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

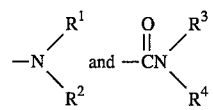

wherein each of $R^1$, $R^2$, $R^3$ and $R^4$ is independently selected from hydrogen and alkyl; or a pharmaceutically-acceptable salt thereof.

Specific compounds of particular interest within Formula XII are the following:

[7-bromo-3-(methoxyphosphonomethyl)imidazo[1,2-a]pyridin-2-yl] phosphonic acid;
[7-bromo-3-(2 -methoxy-2 -phosphonoethyl)imidazo[1,2 -a]pyridin- 2-yl ]phosphonic acid;
(7-chloroimidazo[1,2 -a]pyridin-2,3-diyl]biphosphonic acid;

[7-chloro-3-(phosphonomethyl)imidazo[1,2-a]pyridin-2-yl]phosphonic acid;

[7-chloro-3-(phosphonoethyl)imidazo[1,2-a]pyridin-2-yl]phosphonic acid;

[(7-chloroimidazo[1,2-a]pyridin-2,3-diyl)bis(methylene]biphosphonic acid;

and the pharmaceutically-acceptable salts thereof.

Another more preferred class of compounds within the third subset defined by Formula X consists of compounds of Formula XIII

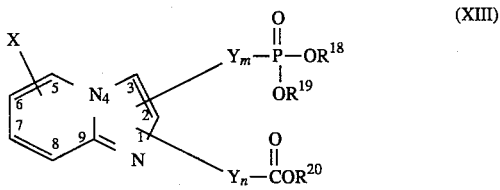

wherein each of $R^{18}$, $R^{19}$ and $R^{20}$ is independently selected from hydrogen, methyl, ethyl, n-propyl, isopropyl, n-butyl, isobutyl, sec-butyl, tert-butyl, cyclopropyl, cyclobutyl, cyclopentyl, cyclohexyl and cycloheptyl;
wherein each of $Y_m$ and $Y_n$ is a spacer group independently selected from one or more methylene or ethylene radicals of the formula

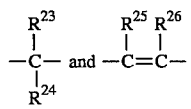

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, alkanoyl,

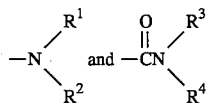

wherein each of $R^1$, $R^2$, $R^3$ and $R^4$ is independently selected from hydrogen and alkyl; wherein $R^{23}$ and $R^{24}$ may be taken together to form oxo; wherein each of $R^{25}$ and $R^{26}$ is independently selected from hydrogen, alkyl, haloalkyl, hydroxyalkyl and alkoxyalkyl; wherein m is an integer of from one to three, inclusive; n is an integer of from zero to three, inclusive;
wherein each X is one or more groups selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

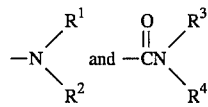

wherein each of $R^1$, $R^2$, $R^3$ and $R^4$ is independently selected from hydrogen and alkyl; or a pharmaceutically-acceptable salt thereof.

Specific compounds of particular interest within Formula XIII are the following:

7-bromo-3-(hydroxylphosphonomethyl)imidazo[1,2-a]pyridine-2-carboxylic acid;

7-bromo-3-(2-hydroxy-2-phosphonoethyl)imidazo[1,2-a]pyridine-2-carboxylic acid;

7-chloro-3-phosphonoimidazo[1,2-a]pyridine-2-carboxylic acid;

7-chloro-3-(phosphonomethyl)imidazo[1,2-a]pyridine-2-carboxylic acid;

7-chloro-3-(2-phosphonoethyl)imidazo[1,2-a]pyridine-2-carboxylic acid;

7-chloro-3-(phosphonomethyl)imidazo[1,2-a]pyridine-2-acetic acid;

and the pharmaceutically-acceptable salts thereof.

The term "hydrogen" denotes a single hydrogen atom (H). This hydrogen group may be attached, for example, to a carbon atom to form a hydrocarbyl group, or attached to an oxygen atom to form a hydroxyl group; or, as another example, two hydrogen groups may be attached to a carbon atom to form a —$CH_2$— group. Where the term "alkyl" is used, either alone or within other terms such as "haloalkyl", "aralkyl" and "hydroxyalkyl", the term "alkyl" embraces linear or branched radicals having from one to about ten carbon atoms. Preferred alkyl radicals are linear or branched "lower alkyl" radicals having from one to about five carbon atoms. Specific examples of alkyl groups are methyl, ethyl, n-propyl, isopropyl, n-butyl, sec-butyl, isobutyl, tert-butyl, n-pentyl, isopentyl and neopentyl. The term "cycloalkyl", embraces radicals having three to ten carbon atoms, such as cyclopropyl and cyclobutyl. The term "haloalkyl" embraces radicals wherein any one or more of the carbon atoms is substituted with one or more halogen groups, preferably selected from bromine, chlorine and fluorine. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups my be substituted with two or more of the same halo groups, or my have a combination of different halo groups. A dihaloalkyl group, for example, may have two bromo atom, such as a dibromomethyl group, or two chloro atoms, such as a dichloromethyl group, or one bromo atom and one chloro atom, such as bromochloromethyl group. Examples of a polyhaloalkyl are trifluoromethyl, 2,2,2-trifluoroethyl, perfluoroethyl and 2,2,3,3-tetrafluoropropyl groups. The term "aryl" embraces aromatic radicals such as phenyl, biphenyl and naphthyl. The term "aralkyl" embraces aryl-substituted alkyl radicals such as benzyl, diphenylmethyl and triphenylmethyl. The terms "benzyl" and "phenylmethyl" are interchangeable. The term "alkoxy" embraces linear or branched oxy-containing radicals having an alkyl portion of from one to about ten carbon atoms, such as methoxy, ethoxy, isopropoxy and butoxy. The term "alkylthio" embraces radicals containing a linear or branched alkyl group of one to about ten carbon atoms attached to a divalent sulfur atom, such as a methythio group. The terms "aryloxy" and "arylthio" denote, respectively, aryl groups having an oxygen or sulfur atom through which the radical is attached to a nucleus, examples of which are phenoxy and phenylthio. The terms "sulfinyl" and "sulfonyl", whether used alone or linked to other terms, denote respectively divalent radicals >SO and >$SO_2$. The term "acyl" whether used alone, or within a term such as acyloxy, denotes a radical provided by the residue remaining after removal of hydroxy from an organic acid, examples of such radical being acetyl and benzoyl. The term "alkenyl" embraces linear or branched radicals having two to about twenty carbon atoms, preferably three to about ten carbon atoms, and containing at least one carbon-carbon double bond, which may have either cis or trans geometry within the alkenyl moiety. The term "alkynyl" embraces linear or branched radicals having two to about twenty carbon atoms, preferably two to about ten carbon atoms, and containing at least one carbon-carbon triple bond. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or alkoxyalkyl" radicals my be further substituted with one or more halo atoms, such as fluoro, chloro or bromo, to provide haloalkoxy or haloalkoxyalkyl groups. The terms "heteroaryl", "aromatic heterocyclic group" and "fully unsaturated heterocyclic group" embrace aromatic ring systems containing one to four hetero atoms selected from oxygen, nitrogen and sulfur in a ring system having five or six ring members which may include the nitrogen atom of an amino or amidoradical (as mentioned in the foregoing description).

Examples of such "heteroaryl" groups are thienyl, furanyl, pyridinyl, thiazolyl, pyrimidyl, isoazolyl and the following structures:

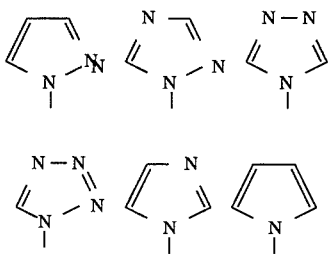

Examples of heterocyclic groups, which may be saturated or partially unsaturated and having five to seven ring members including the nitrogen atom of amino or amido radical (as mentioned in the foregoing description) are the following:

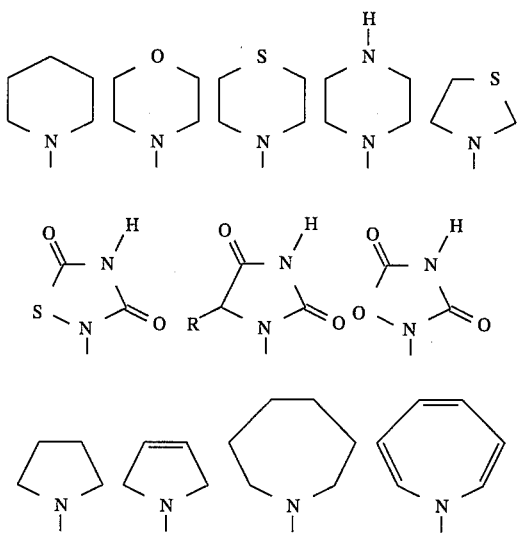

Also embraced within the foregoing definitions are fused ring radicals, i.e., radicals having two or more fused rings either or both of which my be saturated, partially unsaturated or fully unsaturated, examples of which are the following:

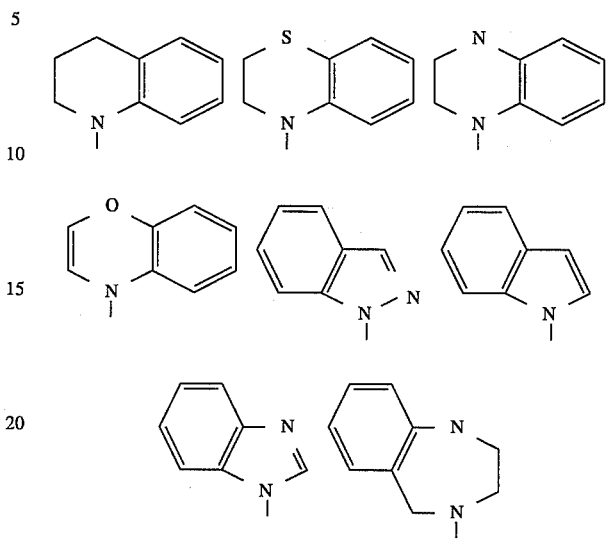

The terms "heteroaryl" and "saturated or partially unsaturated heterocyclic" are also specified as possible selections for the X, and substituents of Formula I compounds of this invention. Examples of such terms are as illustrated above for the hetero-containing groups which incorporate an amino or amido radical nitrogen atom within the heteroaryl or heterocyclic group. Where the terms "heteroaryl" and "saturated or partially unsaturated heterocyclic" are specified as selections for X, it is understood that such terms are construed in light of the foregoing description and exemplifications (with the exception that any of the specified groups may be attached at the X, Y and T positions any attachable position on the group, including the amino or amido radical nitrogen atom). Any of these groups may be attached at the X, Y and T positions through an alkyl group. Thus, "heteroarylalkyl" would be exemplified by imidazolemethyl.

Within this class of compounds of the invention are the pharmaceutically-acceptable salts of the compounds of Formula I, including acid addition salts and base addition salts. The term "pharmaceutically-acceptable salts" embraces "pharmacologically-acceptable salts" commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids my be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts my be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

Compounds of general Formula I can exist in the form of tautomers, e.g. tautomers of tetrazoles. Thus, tautomers of the compounds of general Formula I are also within the scope of the present invention.

General Synthetic Procedures

Compounds embraced by Formula I may be prepared in accordance with Schemes I–III which follow:

Scheme I:

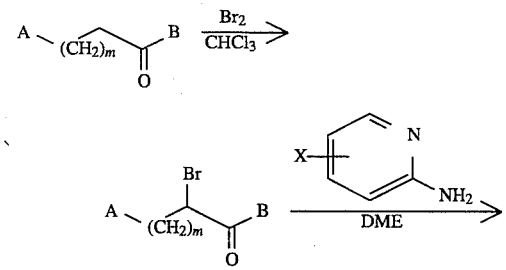

-continued
Scheme I:

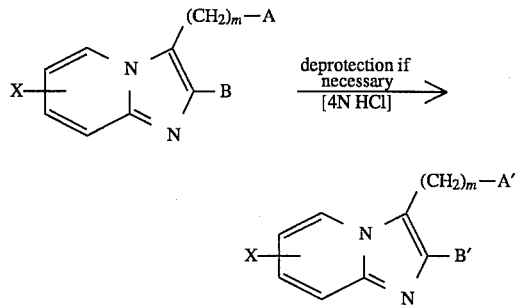

A' & B' = independently, tetrazole,? $CO_2H$, $PO_3H_2$?
m = 1–5?

Scheme II:

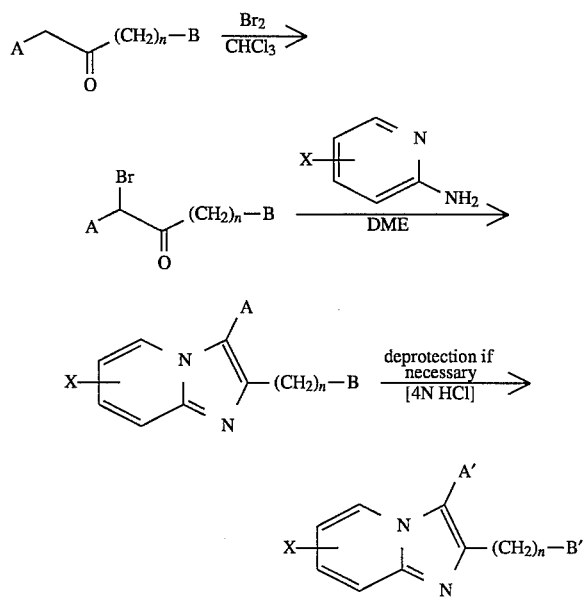

A' & B' = independently, tetrazole,? $CO_2H$, $PO_3H_2$?
n = 0–5?

Scheme III:

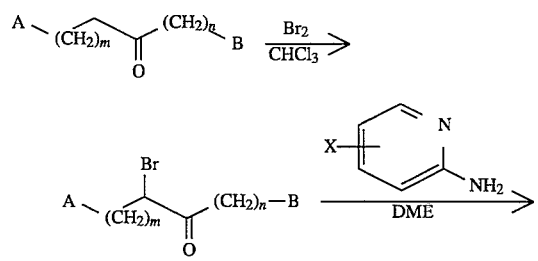

-continued
Scheme III:

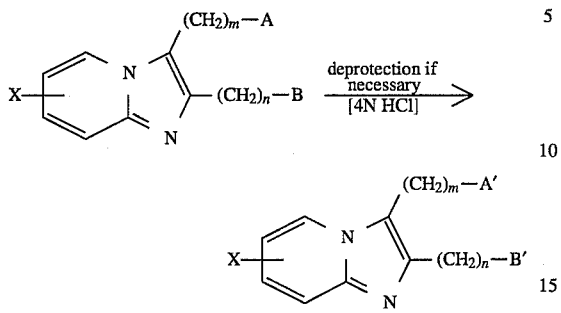

A' & B' = independently, tetrazole,?
CO₂H, PO₃H₂;?
m = 1-5?
n = 0-5?

The following Examples are detailed descriptions of the methods of preparation of compounds of Formula I. These detailed preparations fall within the scope of, and serve to exemplify, the above described General Synthetic Procedures which form part of the invention. These Examples are presented for illustrative purposes only and are not intended as a restriction on the scope of the invention. All parts are by weight unless otherwise indicated. Most of the commercially-available starting materials were obtained from Aldrich Chemical Co., Milwaukee, Wis.

EXAMPLE 1

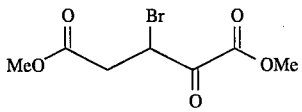

2-Bromo-α-ketoglutaric acid dimethyl ester

To a stirred solution of α-ketoglutaric acid dimethyl ester (5 g, 0.03 mol) in CHCl₃ (25 mL) was added bromine (5.2 g, 0.06 mol). The reaction was heated to reflux for 3 h. After cooling to room temperature, all solvent was removed in vacuo to leave desired title compound.

EXAMPLE 2

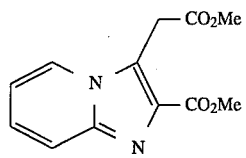

Methyl 3-(methoxycarbonyl)imidazo[1,2-a]pyridine-3-acetate

To a stirred solution of 2-aminopyridine (0.372 g, 3.95 mmol) in ethylene glycol dimethyl ether (30 mL) under N₂ was added the 2-Bromo-α-ketoglutaric acid dimethyl ester product of Example 1 (1.0 g, 0.95 mol). The reaction was stirred at room temperature overnight. Absolute ethanol (EtOH, 15 mL) was added to the oil precipitate and the resulting solution heated to reflux for 4 h. All solvent was removed in vacuo. To the resulting residue was added aq K₂CO₃ and the product was extracted into ethyl acetate. The organic extracts were then dried (MgSO₄), treated with decolorizing charcoal, filtered and all solvent was removed in vacuo. Chromatography using a 98/1/1 CH₂Cl₂/EtOH/ NH₄OH mobile phase yielded clean title compound. Anal. Calcd for $C_{12}H_{12}N_2O_4$: C, 58.06; H, 4,87; N, 11.29. Found: C, 57.74; H, 4.88; N, 11.15. ¹H NMR (300 MHz, CDCl³): 3.75 (3H,s), 4 (3H, s), 4.5 (2H, s), 6.93 (1H, t, J=6.7 Hz), 7.3 (1H, t, J=7.h Hz), 7.7 (1H, d, J=8 Hz), 8 (1H,d, 5Hz).

EXAMPLE 3

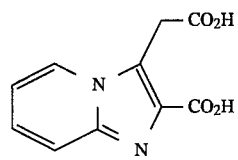

3-carboxyimidazo[1,2-a]pyridine-3-acetic acid, hydrochloride

The imidazopyridine ester product of Example 2 (0.057 g, 0.23 mmol) was dissolved in 4N HCl (4mL) and heated to reflux for 14 h. All solvent was removed in vacuo and the residue triturated with diethyl ether to yield clean title compound (0.021 g, 51%). Anal. Calcd for $C_{11}H_8N_2O_4 \cdot 1.1$ HCl·0.9 H₂O: C, 43.44; H, 3.97; N, 10.13; $C_{1,\ 14.10}$. Found: C, 43.32; H, 3.60; N, 10.18; $C_{1,\ 14.22}$. ¹H NMR (300 MHz, DMSO): 4.5 (2H, s), 7.5 (1H, t, J=6.25 Hz), 7.95 (2H, m), 9 (1H, d, J=12.5 Hz).

BIOLOGICAL EVALUATION

Glutamate Binding Assays

The purpose of this assay is to determine the binding affinity of a compound of Formula I for the N-methyl-D-aspartate (NMDA) receptor site. This procedure was carried out as follows:

Synaptic plasma membranes (SPM) were prepared as previously described [Monaban, J. B. and Michel, J., "Identification and Characterization of an N-methyl-D-aspartate-specific L-[3H]glutamate Recognition Site in Synaptic Plasma Membranes, *J. Neurochem.*, 48, 1699–1708 (1987)]. The SPM were stored at a concentration of 10–15 mg/mL in 0.32M sucrose, 0.5 mM EDTA, 1 mM MgSO₄, 5 mM Tris/SO₄, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins Using the Biuret and Phenol Reagents", *Anal. Biochem.*, 86, 193–197 (1978)]. The SPM were thawed at room temperature, diluted twenty-fold with 50 mM tris/acetate, pH 7.4, incubated at 37° C. for 30 minutes, and centrifuged at 100,000 g for 15 minutes. The dilution, incubation, and centrifugation was repeated a total of three times. This general method involved adding 12.5 nM of the L-[3H]glutamate radioligand to the appropriate concentration of the test compound and initiating the assay by the addition of ice cold SPM (0.2–0.45 mg). The binding assays were performed in 1.5 mL centrifuge tubes with the total volume adjusted to 1.0 mL. Additions of test compounds were made in 50 mM Tris/acetate, pH 7.4 and incubations were carried out at 0°–4° C. The incubation time for the NMDA binding assay was 10 minutes. To terminate the incubation, the samples were centrifuged for 15 minutes at 12,000 g and 4° C. in a Beckman Microfuge 12. The supernatant was aspirated and the pelleted membranes dissolved in Beckman Ready-Protein scintillation cocktail. The samples counted on a Beckman LS 5800 or 3801 liquid scintillation counter with automatic corrections for quenching and counting efficiency. Nonspecific binding was defined as the residual binding in the presence of 0.5 mM NMDA and was typically 15–25% of the total binding in the NMDA binding assay. Radioligand binding to the SPM was analyzed using Scatchard and Hill transformations and the $K_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", *Computer Appln. Biosci.*, 3 131 (1987)]. Binding results are reported in Table I for example compounds of the invention.

Glycine Binding Assay Procedure

Synaptic plasma membranes (SPM) were prepared from rat forebrain and stored as previously described [J. B. Monahan and J. Michel, *J. Neurochem.*, 48, 1699–1708 (1987)]. Frozen membranes were thawed and diluted 1:20 with 0.04% Triton X-100 in 50 mM tris/acetate (pH 7.4). Following incubation at 37° C. for 30 min., the SPM were collected by centrifugation at 95,000×g for 15 min. The pellet was resuspended in 50 mM tris/acetate (pH 7.4, Triton-free) and hand-homogenized five times. The membranes were again centrifuged as above. The pellet was washed two additional times with 50 mM tris/acetate (without homogenization) and centrifuged. The final pellet was resuspended with homogenization in 50 mM tris/acetate. In the general receptor binding assay procedure, 10 nM [3H] glycine was added to the appropriate concentration of the test compounds and the assay initiated by the addition of 0.2–0.4 mg of ice cold SPM. The assay, which was done in 1.5 mL centrifuge tubes, was adjusted to a total volume of 1.0 mL with all additions being made in 50 mM tris/acetate, pH 7.4 at 4° C. After a 10 minute incubation at 2° C., the samples were centrifuged for 15 min. at 12,000 g (4° C.) in a Beckman Microfuge 12. The supernatant was aspirated and the tube tip containing the pelleted membranes cut off and agitated in 0.5 mL of Beckman BTS-450 tissue solubilizer for a minimum of 6 hours at room temperature. Beckman MP scintillation cocktail (5 mL) containing 7 mL/liter acetic acid was then added and the samples counted on a Beckman LS 5800 liquid scintillation counter with automatic corrections for quenching and counting efficiency. Nonspecific binding was defined as the residual binding in the presence of 0.1 mM glycine and usually amounted to 25–35% of the total binding. The binding of [3H]glycine to the SPM was analyzed using Scatchard and Hill transformations and the Ki for other compounds was determined using logit-log analysis. Calculations and regression analysis were performed using templates developed for Lotus 123 as previously described [Pullan et al, Id.]. Binding results are reported in Table I, for example compounds of the invention.

TCP Modulating Assay

The effect on the TCP (1-[1-(2-thienyl)cyclohexyl] piperidine) binding was measured in rat brain synaptic membranes (SPM) prepared as previously described [J. B. Monahan & J. Michel; *J. Neurochem.* 48, 1699–1708 (1987)]. Prior to their use in the binding assay, frozen SPM were thawed, diluted twenty fold with 50 mM tris/acetate (pH 7.4 containing 0.04% (v/v) Triton X-100), incubated for 30 min. at 37° C. and centrifuged at 95,000×g for 15 min. The Triton X-100 treated SPM were washed with 5 mM tris/HCl, pH 7.4 and centrifuged a total of six times. The compound of Example 3 was incubated at different concentrations with SPM (0.2–0.4 mg protein) and 2 nM [3H]TCP, in a total volume of 0.5 mL of 5 mM tris/HCl buffer pH 7.4 at 25° C. for 60 min. The samples were filtered through glass fiber filters (Schleicher & Schuell #32) which have been pre-treated with 0.05% (v/v) polyethylenimine, washed 4 times with 2 mL of ice-cold 5 mM Tris/HCl buffer, and then counted on a Beckman LS 5800 liquid scintillation counter with automatic corrections for quenching and counting efficiency. Inhibition of TCP binding was measured as a decrease in the binding in the presence of 0.05 µM L-glutamate. Non-specific binding was defined as the residual binding in the presence of 60 µM phencyclidine. Results are shown in Table I.

TABLE I

| | Receptor Binding Data (IC$_{50}$) | | | |
|---|---|---|---|---|
| Compound Ex. # | [3H]GLY $K_i$(µM) | [3H]GLU $K_i$(µM) | KA $K_i$(µM) | [3H]TCP INHIB. |
| 3 | 51 | 15.9 | 51 | 26% @ 66 µM |

Results and Discussion

Using the foregoing TCP Modulation Assay, a study was made of the effect of increasing concentration of Example #3 compound on inhibition of [3H]TCP modulation in the presence of various fixed concentrations of glutamate. Results are shown in Table II.

TABLE II

Effect of increasing glutamate concentration on Example #3 compound inhibition of [3H]TCP modulation.

| Ex. #3 compound | Glutamate (µM) | | | |
|---|---|---|---|---|
| (µM) | 0 | 0.05 µM | 0.2 µM | 1 µM |
| 0 | 3648 (24) | 6822 (45) | 11671 (77) | 15222 (100) |
| 6 | 4363 (29) | 7680 (50) | 11660 (77) | 14275 (94) |
| 20 | 5082 (33) | 8011 (53) | 11183 (73) | 13870 (91) |
| 60 | 8144 (54) | 8601 (57) | 10568 (69) | 13555 (89) |
| 120 | 9598 (63) | 10897 (72) | 11278 (74) | 13461 (88) |
| 200 | 10336 (68) | 10307 (68) | 11476 (75) | 13433 (88) |
| 400 | 9860 (65) | 9777 (64) | 10602 (70) | 11215 (74) |
| 660 | 7672 (50) | 8342 (55) | 7871 (52) | 7809 (51) |

Data is expressed as dpm [3H]TCP binding, with the percent of maximal glutamate (1 µM) stimulated [3H]TCP binding in the absence of Ex #3 compound shown in parentheses.

The ability of a compound to modulate [3H]TCP binding in rat brain SPM has been shown to correspond with its effect on NMDA receptor activation state, where NMDA receptor complex agonists stimulate binding and antagonists inhibit binding. The above experiment demonstrates the effect of Example #3 compound on [3H]TCP binding in the presence of several fixed concentrations of the NMDA receptor agonist, L-glutamate. As shown in Table II and in FIG. 1, these results indicate that, depending on the concentrations tested, Example #3 compound has both NMDA agonist and antagonist properties (i.e., can both increase and, at higher concentrations, decrease [³H]TCP binding. This data is consistent with Example #3 compound acting through two sites to obtain the observed effects. At low concentrations (<200 μM), Example #3 compound behaves as a partial agonist while at higher concentrations it has antagonist actions. The specific sites of these actions support the proposition that Example #3 compound interacts at both the NMDA and, at higher concentrations, the glycine recognition sites. If Example #3 compound actions are limited to these two sites it would be reasonable to conclude that the partial agonist effect is mediated through the NMDA recognition site and the antagonist effect through the glycine site based on potency.

Based on these observations, it is believed that compounds of the invention would be useful at higher concentrations to treat neurotoxic injury and also would be useful at lower concentrations to treat cognitive disorders or to use as a cognitive enhancer.

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple subdoses per day. These subdoses may be administered in unit dosage forms. Typically, a dose or subdose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations my be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of Formula III

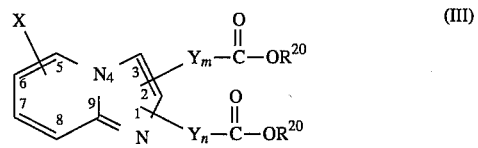

wherein each $R^{20}$ is independently selected from hydrogen, alkyl, allyl, cycloalkyl, cycloalkylalkyl, phenyl and benzyl; wherein each of $Y_m$ and $Y_n$ is a spacer group independently selected from one or more groups of the formula

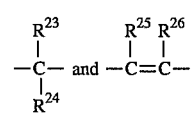

wherein each of $R^{23}$ and $R^{24}$ is independently selected from hydrogen, alkyl, cycloalkyl, halo, haloalkyl, hydroxy, hydroxyalkyl, alkoxy, alkoxyalkyl, and alkanoyl;
wherein $R^{23}$ and $R^{24}$ may be taken together to form oxo;
wherein each of $R^{25}$ and $R^{26}$ is independently selected from hydrogen, alkyl, haloalkyl, hydroxyalkyl and alkoxyalkyl; m is an integer of from one to three, inclusive; n is an integer of from zero to three, inclusive;
wherein X is one or more groups independently selected from hydrogen, alkyl, cycloalkyl, halo, haloalkyl, phenyl, benzyl, hydroxy, hydroxyalkyl, alkoxy, phenoxy, alkoxyalkyl, benzyloxy, alkanoyl,

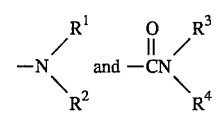

wherein each of $R^1$, $R^2$, $R^3$ and $R^4$ is independently selected from hydrogen and alkyl; or a pharmaceutically-acceptable salt thereof.

2. Compound of claim 1 selected from the group consisting of
  7-bromo-2-carboxy-α-methoxyimidazo[1,2-a]pyridine-3-acetic acid;
  7-bromo-2-carboxy-α-methoxyimidazo[1,2-a]pyridine-3-propanoic acid;
  2-carboxy-7-chloroimidazo[1,2-a]pyridine-3-acetic acid;
  2-carboxy-7-chloroimidazo[1,2-a]pyridine-3-propanoic acid; and
  7-chloroimidazo[1,2-a]pyridine-2,3-diacetic acid.

3. A pharmaceutical composition comprising a therapeutically-effective amount of an active compound and a pharmaceutically-acceptable carrier or diluent, said active compound selected from a compound of claim 1.

4. A method to treat or prevent excitatory amino acid induced neurotoxic injury mediated by the NMDA receptor in a subject, which method comprises administering to said subject a therapeutically-effective amount of a compound of claims 1 or 2.

* * * * *